(12) United States Patent
Wernz et al.

(10) Patent No.: US 8,376,863 B2
(45) Date of Patent: Feb. 19, 2013

(54) TORQUE LIMITER

(75) Inventors: Ulrich Wernz, Tuttlingen-Nendingen (DE); Stephan Siebold, Muehlheim (DE)

(73) Assignee: W + S Solutions GmbH, Tuttlingen-Nendingen (DE)

( * ) Notice: Subject to any disclaimer, the term of this patent is extended or adjusted under 35 U.S.C. 154(b) by 171 days.

(21) Appl. No.: 12/903,293

(22) Filed: Oct. 13, 2010

(65) Prior Publication Data

US 2011/0092295 A1   Apr. 21, 2011

(30) Foreign Application Priority Data

Oct. 15, 2009   (EP) .................................... 09013065

(51) Int. Cl.
*F16D 7/10*   (2006.01)
(52) U.S. Cl. ........................................................ 464/37
(58) Field of Classification Search .................. 464/34, 464/35, 37, 41
See application file for complete search history.

(56) References Cited

U.S. PATENT DOCUMENTS

| | | | |
|---|---|---|---|
| 2,344,673 A * | 3/1944 | Brown | 464/37 |
| 2,930,212 A * | 3/1960 | Walterscheid-Muller et al. | 464/37 |
| 5,366,412 A | 11/1994 | Beaty et al. | |
| 5,390,573 A | 2/1995 | Mann | |
| 5,517,742 A | 5/1996 | Mann | |
| 5,924,864 A | 7/1999 | Loge et al. | |
| 6,012,985 A * | 1/2000 | Sukup | 464/37 |
| 2007/0209486 A1 | 9/2007 | Gauthier et al. | |
| 2009/0192501 A1 | 7/2009 | Miletto et al. | |

FOREIGN PATENT DOCUMENTS

| | | | |
|---|---|---|---|
| CA | 2637284 A1 | | 9/2007 |
| DE | 1 216 622 | * | 5/1966 |
| DE | 4414963 A1 | | 11/1994 |
| DE | 202006004027 U1 | | 6/2006 |
| DE | 102007051263 A1 | | 4/2009 |
| EP | 0873724 A1 | | 10/1998 |
| EP | 1110512 A1 | | 6/2001 |
| EP | 2085041 A1 | | 8/2009 |
| GB | 876592 | * | 9/1961 |
| GB | 2191128 A | | 12/1987 |
| WO | 2008/075186 A2 | | 6/2008 |

* cited by examiner

*Primary Examiner* — Gregory Binda
(74) *Attorney, Agent, or Firm* — Bachman & LaPointe, P.C.

(57) ABSTRACT

A torque limiter, in particular for a surgical instrument, comprises a rotor (4) and a cage (8) arranged coaxially in relation to the rotor (4), the cage has at least one rolling body holder (7) with a rolling body (6) held in it, the rolling body holder (7) has at least one side wall which is arranged at an oblique angle relative to a circumferential direction of the cage (8).

8 Claims, 3 Drawing Sheets

TORQUE LIMITER

FIELD OF THE INVENTION

The invention relates to a torque limiter, in particular for a surgical instrument, a method for producing the torque limiter and an assembly kit for the torque limiter.

BACKGROUND OF THE INVENTION

In surgery, screws or other components often have to be tightened with a defined torque. In such cases, a maximum torque in the direction of the tightening of the screw must not be exceeded in order to avoid damage to the components or to bones. On the other hand, loosening of the screw should be possible, including with a higher torque, in order for it to be possible in the event of a seized screw to remove it again from the body. For this reason, torque limiters such as are used in surgery are fundamentally different from torque limiters such as are used generally in mechanics, since in the case of the latter a freewheel is usually arranged in the opposite direction.

There are torque limiters known from the prior art that operate with an elastic body which can transmit a torque from an inner shaft to an outer rotor. For instance, European Patent Application EP 2 085 041 A1 relates to a corresponding surgical instrument. It is disadvantageous, however, that the maximum torque is determined by the elastic body. Furthermore, fatigue of the synthetic materials of the elastic body may bring about a change in the properties of the instrument. This is disadvantageous, since the maximum transmissible torque can change.

SUMMARY OF THE INVENTION

An object of the invention is to eliminate, or at least mitigate, the disadvantages of the prior art described above and provide an improved torque limiter, a method for producing an improved torque limiter and an assembly kit for an improved torque limiter. In particular, an object of the invention is to develop a torque limiter or a corresponding assembly kit which can be adapted to different maximum torques to be transmitted and which exhibit reduced changing of the mechanical properties over time.

A torque limiter, particularly for surgical instruments, a method for producing a corresponding torque limiter and an assembly kit for a torque limiter are provided to achieve the object. By providing an inclined plane as a guide for a rolling body, a certain resistance to displacements of the rolling body along the oblique plane can be achieved by choosing the angular position of the inclination. Furthermore, a maximum transmissible torque can be chosen or set by choosing the number of rolling bodies held in the cage. In this way, a maximum transmissible torque can be chosen by simple means. It should be noted that, opposite the side wall that is arranged at an oblique angle to a circumferential direction of the cage, there is preferably arranged a second side wall, which is parallel to this first side wall and together with the first side wall forms the rolling body holder. This achieves the effect that, depending on the direction of rotation of the cage in relation to the rotor, a displacement of the rolling body in the rolling body holder is opposed with a different resistance, since the equilibrium of forces at the point of contact of the rolling body on the side wall differs according to the direction of rotation. The consequence is that a maximum transmissible torque can be transmitted in one direction and a virtually unlimited torque, or at least a torque that is increased significantly in comparison with the above-named maximum torque, can be transmitted in the other direction. This achieves the effect that a seized screw can in any event be loosened.

The cage is preferably formed as a tube and arranged coaxially in relation to the rotor. The side wall or the two side walls that form the rolling body holder are accordingly tilted with respect to a radial direction of the tubular cage, preferably by at least 5°, more preferably by at least 10° or at least 20°. The angle with respect to the radial is preferably less than 70°, more preferably less than 50° and still more preferably less than 35°.

Preferably formed in the rotor is a depression, which is provided for the purpose of interacting with the rolling body. The depression brings about the effect that, when there is rotation of the rotor in relation to the cage, the rolling body must be raised out of this depression, it sliding along on one of the side walls or on the leading one of the side walls of the rolling body holder. The depression is preferably formed as a longitudinal groove in the rotor. Advantageously, a number of depressions are arranged around the rotor, preferably a number of longitudinal grooves, which are arranged just a small distance from one another or no distance at all from one another. The preferred inclination of one or both side walls described above has the effect that there is virtually no friction, or little friction, in one direction of rotation of the cage and appreciable friction in the opposite direction when the rolling bodies are forced out. This achieves the result that torques of different magnitudes can be transmitted.

Preferred embodiments of the invention comprise a pressure-exerting element for pressing the rolling body against the rotor. The pressure-exerting element or the pressure-exerting elements serve(s) the purpose of pressing a rolling body into a depression, so that a force must be expended when a rolling body is forced out of a depression when there is rotation of the rotor with respect to the cage. Whenever reference is made to a single item, for example the pressure-exerting element or the rolling body or the depression, this expressly also includes embodiments which have a plurality of the respective features. In the case of preferred embodiments, the invention also offers the advantage that a maximum admissible torque can be easily and reliably determined by choosing a specific number of rolling bodies, choosing a specific number of pressure-exerting elements or else choosing specific pressure-exerting elements with specific mechanical properties. Advantageous embodiments have a longitudinal groove as the depression or rolling bodies that are formed as rollers.

The pressure-exerting element is preferably circular and also advantageously arranged coaxially in relation to the rotor. The pressure-exerting element may be arranged inside or outside the cage, the rotor preferably being arranged on the opposite side of the cage. This offers a construction that is as simple and compact as possible. Particular advantages are offered by an inner pressure-exerting element, which is arranged inside the cage. If the pressure-exerting element is arranged outside the cage and the rotor inside the cage, the pressure-exerting element may be formed as a ring.

The pressure-exerting element is preferably a rubber ring or a circumferentially extending garter spring or a spring washer or a lock washer or a radially arranged spiral spring. Preferred embodiments also comprise in each case a number of these pressure-exerting elements or various of these pressure-exerting elements, for example in order to achieve an increase in the maximum transmissible torque.

A pressure-exerting element formed as a spring washer preferably has spring arms which extend substantially in the circumferential direction on the spring washer. Here, "substantially" preferably means that the spring arms are separated from the rest of the spring washer by a groove extending approximately in the circumferential direction, i.e. with an angle of at most 20° or 10° with respect to the circumferential direction or exactly in the circumferential direction. This offers the advantage that the spring arms act in the direction of pressing the rolling body against the rotor. In the case of typical embodiments, the spring arms are preferably arranged spirally at an angle of between 0° and 20° in relation to the circumferential direction. In this way, the spring arm is accommodated with an adequate spring length in a small space.

The cage and the spring washer are advantageously held in a fixed angular position in relation to one another by an anti-rotation element. In this way it is ensured that the spring arms of the spring washer act on the rolling bodies at exactly defined pressure-exerting points. This avoids changing of the mechanical advantage obtained in the direction of effect of a spring arm when there is rotation of the cage with respect to the spring washer. In this way it is ensured that pressure is exerted on the rolling bodies with a defined force.

The anti-rotation element preferably comprises a groove which interacts with a cam. The cam is preferably arranged on the spring washer. The groove is preferably arranged in the cage. It is also possible for a number of grooves and cams to be provided, distributed over the circumference of the spring washer or the cage. Similarly, a converse arrangement is possible, that is to say grooves in the spring washer and cams on the cage. Grooves in the cage have the advantage that the weight of the cage is reduced. The grooves and cams achieve the effect that the lock washer can be easily pushed onto the cage in a specific position that is optimized for operation.

In the case of preferred embodiments of the invention, the cage has a plurality of rolling body holders, rolling bodies not being provided in all the rolling body holders. The number of rolling bodies is accordingly preferably less than the number of rolling body holders. In this way, a reduction in the maximum transmissible torque to a desired level is achieved.

A further aspect of the invention relates to a method for producing a torque limiter in one of the preferred embodiments described above, a maximum torque that can be transmitted by the torque limiter in one direction of rotation being set by choosing a specific number of rolling bodies that are fitted in the rolling body holder or choosing the type or number of pressure-exerting elements that are installed in the torque limiter. Here, type of pressure-exerting elements means that differently formed spring washers or rubber rings or garter springs can be used. For instance, thicker and thinner spring washers may be used, the thinner spring washers producing a lower contact pressure than the thicker spring washers. Similarly, the spring arms of different spring washers may be differently configured, in order to achieve different pressing forces. In the case of preferred production methods, the number of rolling bodies used is determined on the basis of a maximum torque to be transmitted in one direction of rotation. It is similarly preferred to choose the type or number of pressure-exerting elements on the basis of the maximum transmissible torque required.

A further aspect of the invention relates to an assembly kit for a torque limiter, in particular in one of the preferred embodiments described above. The assembly kit offers the particular advantage that a maximum transmissible torque can be set by the user simply by choosing specific categorized components, such as rolling bodies or pressure-exerting elements. Furthermore, a torque limiter according to the invention or a corresponding assembly kit offers the advantage that it is easily completely sterilizable. A preferred assembly kit comprises at least two rolling bodies and a cage with at least two rolling body holders. The user can choose a maximum transmissible torque by choosing the parts, such as the number of rolling bodies or pressure-exerting elements. Similarly, three or more rolling body holders and rolling bodies may preferably constitute part of the assembly kit. Furthermore, it is preferred that the assembly kit comprises at least two pressure-exerting elements. A maximum transmissible torque can be set by choosing the number of pressure-exerting elements that are later used in the torque limiter. Furthermore, it is preferred that the assembly kit comprises at least two different pressure-exerting elements. In this way, different maximum transmissible torques can be chosen.

BRIEF DESCRIPTION OF THE DRAWINGS

A preferred exemplary embodiment of the invention is described below on the basis of the accompanying drawings, in which.

DETAILED DESCRIPTION

Figure 1:
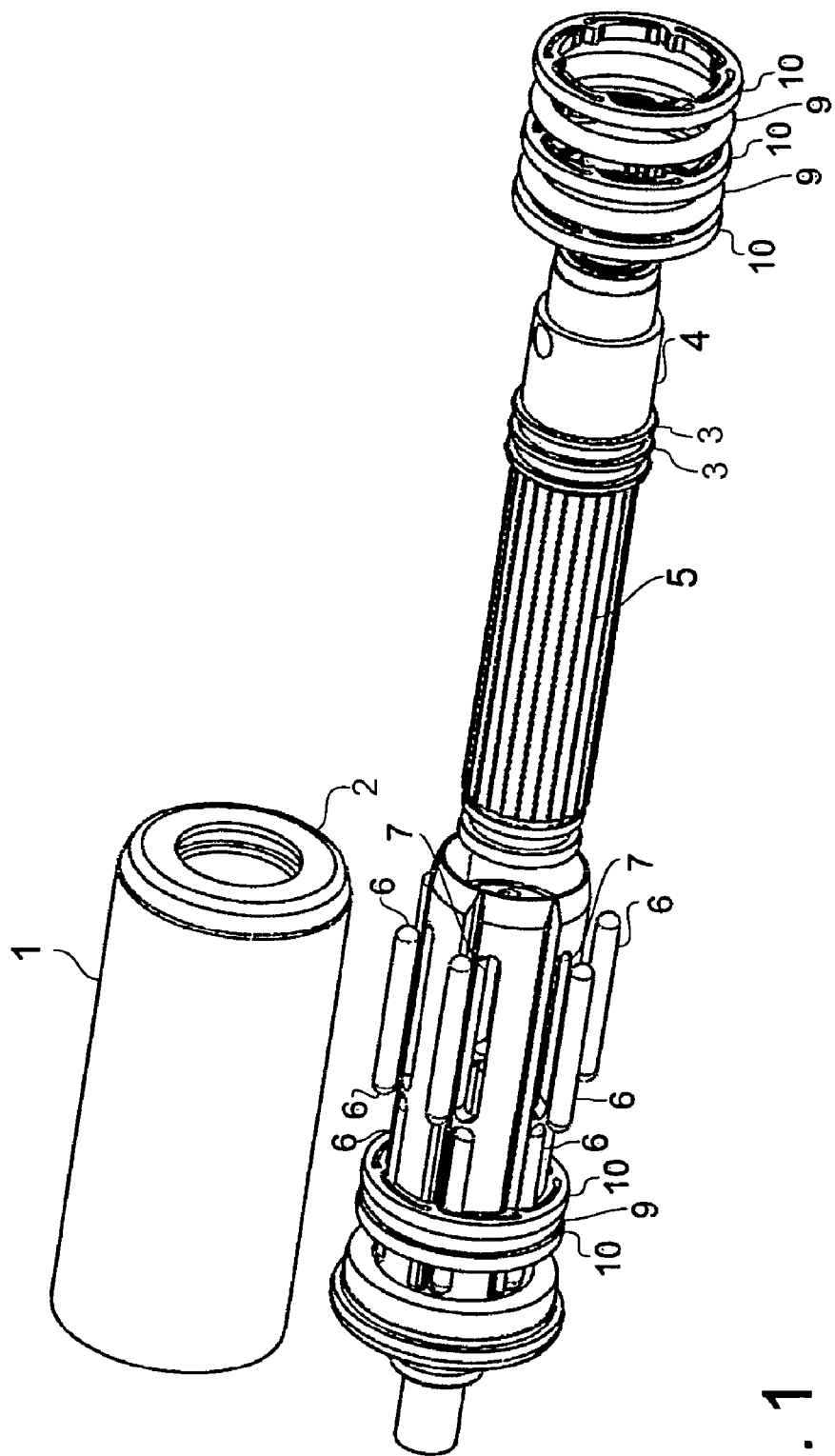
FIG. 1 shows an exploded representation of a torque limiter according to the invention in a schematic perspective view.

FIG. 1 perspectively shows in a schematic exploded representation a torque limiter according to the invention or an assembly kit according to the invention for a torque limiter. The torque limiter has an outer protective sleeve 1, a covering cap 2 and a number of bearings, of which at least one bearing 3 is shown in FIG. 1. The drive output shaft of the torque limiter is formed integrally by an inner rotor 4, on the outer side of which longitudinal grooves are arranged as depressions 5. The longitudinal grooves as depressions 5 are provided for the purpose of interacting with rolling bodies 6, the inner radius of the longitudinal grooves corresponding to the outer radius of the rolling bodies 6. Rollers rounded at the ends are provided as rolling bodies 6. In the case of other typical embodiments, rollers that have sharp-edged ends are provided. The rolling bodies 6 are held in rolling body holders 7 of a cage 8. The cage 8 at the same time forms a drive input shaft of the torque limiter. It goes without saying that the drive input and output of the torque limiter can similarly be changed over.

The rolling bodies 6 are held in the rolling body holders 7 by pressure-exerting elements. Rubber rings 9 and spring washers 10 are used as pressure-exerting elements. It should be noted that, in the exemplary embodiment represented, the rubber rings 9 have scarcely any effect or no effect on the transmissible torque, since the spring washers 10 are significantly more rigid. However, the rubber rings 9 also facilitate the fitting of the rolling bodies 6 in the cage 8, since the rubber rings 9 secure the rolling bodies 6 against falling out. The pressure-exerting elements exert a radial force on the rolling bodies 6, and consequently press the rolling bodies 6 into the rolling body holders 7 against the rotor 4. In a position with minimized energy of the pressure-exerting elements, the rolling bodies 6 are in each case arranged in a depression 5, i.e. a longitudinal groove, of the rotor 4.

When there is relative rotation of the cage 8 with respect to the rotor 4, the rolling bodies 6 must therefore be pressed against the force of the pressure-exerting elements, i.e. the rubber rings 9 and the spring washers 10, so that the rolling bodies 6 can pass from one depression 5 into a next depression 5 of the rotor 4. Another factor here is that the side walls of the rolling body holders 7 are not formed exactly radially in the cage 8, but are arranged at an oblique angle to the surface of the cage 8. As a result, raising of the rolling bodies 6 in the rolling body holders 7 is made easier when there is rotation of the rotor 4 with respect to the cage 8 in one relative direction of rotation than in the opposite direction of rotation. This means that a smaller torque has to be applied in one direction of rotation to rotate the rotor 4 with respect to the cage 8 than in the opposite direction of rotation. The obliquely arranged side walls of the rolling body holders 7 are explained in conjunction with FIGS. 2 and 3.

Figure 2:
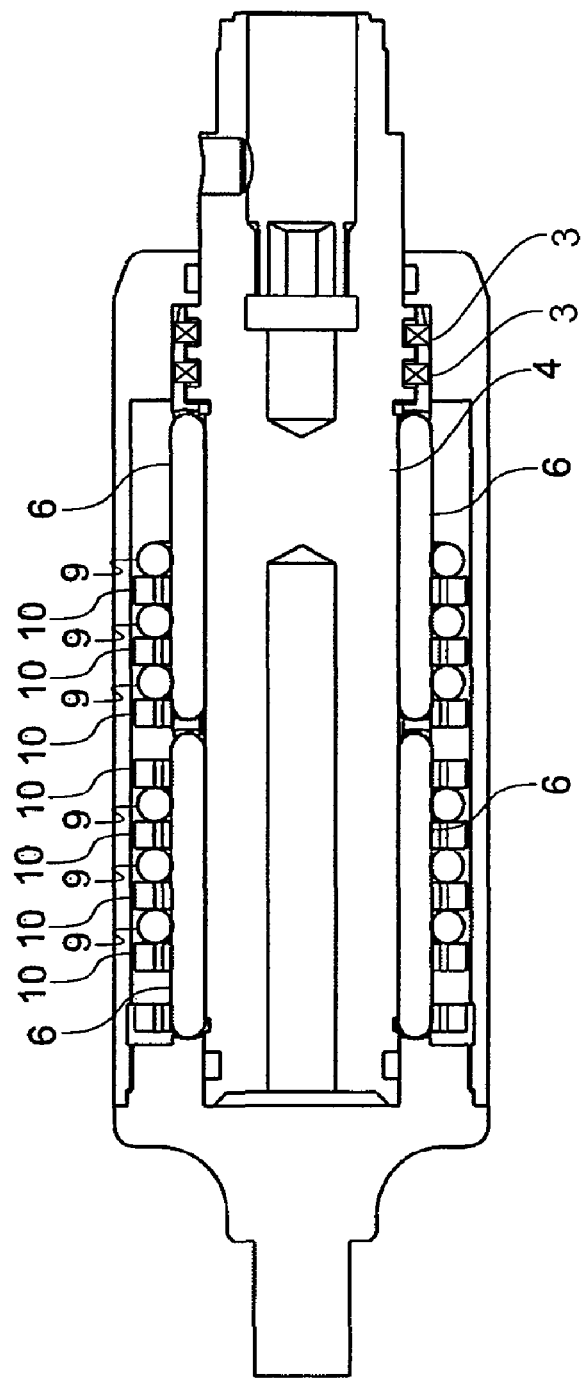
FIG. 2 shows part of the torque limiter of FIG. 1 in the assembled form in a sectional schematic view, the section being chosen along the longitudinal axis of the torque limiter according to the invention.
Figure 3:
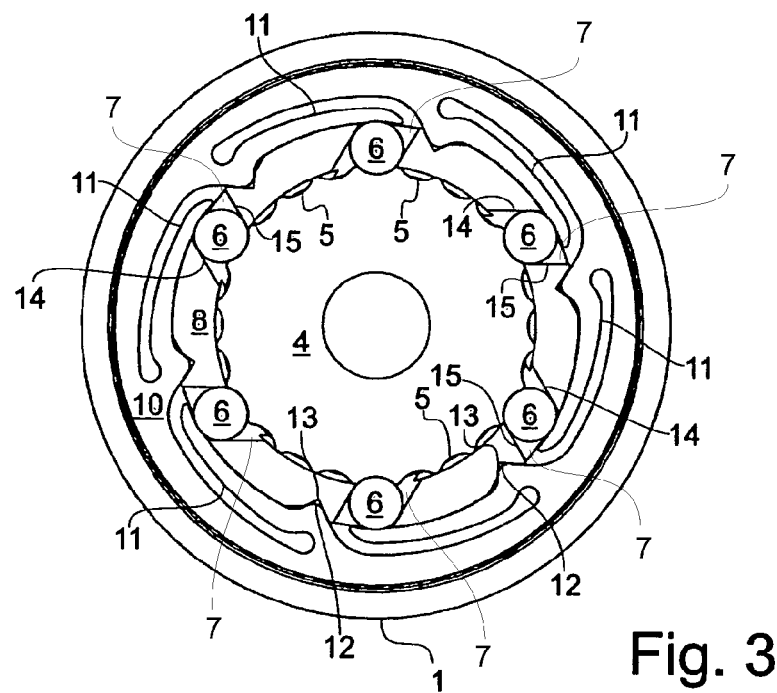
FIG. 3 shows a cross section through the assembled torque limiter with components that are shown in FIG. 1.

It should be noted that the same designations are used for the same or similar parts in FIGS. 1 to 3, and that, in order to improve overall clarity, each part is not provided with a designation in every drawing.

FIG. 2 shows a longitudinal section through an assembled torque limiter. For purposes of explanation, reference is made to the description relating to FIG. 1. It should be noted that, in the case of an assembly of the torque limiter, not all the rolling body holders 7 have to be occupied with rolling bodies 6. It can similarly be seen in FIG. 2 that not all the rolling bodies 6 are in each case pressed by pressure-exerting elements against the rotor 4. It is possible to provide still further pressure-exerting elements in order to increase a torque that can be transmitted as a maximum by the torque limiter. It is similarly possible to omit some of the rubber rings 9 or the spring washers 10 in order to reduce a maximum transmissible torque.

FIG. 3 shows a cross section through the torque limiter according to the invention, the section being arranged level with one of the spring washers 10 (see FIG. 2). For the purposes of explanation, reference is once again made to FIGS. 1 and 2 and the associated descriptions of the figures. Also shown in FIG. 3 are spring arms 11 of the spring washer 10, which, as a spring, press the rolling bodies 6 against the rotor 4.

Also arranged on the spring washers 10 are cams 12, which engage in grooves 13 of the cage 8. The grooves 13 and the cams 12 serve the purpose of producing an anti-rotation element between the spring washer 10 and the cage 8. In this way it is ensured that the contact between the rolling bodies 6 and the spring arms 11 is established at specific points or specific regions of the spring arms 11. In this way the effect is achieved that the rolling bodies 6 are pressed against the rotor 4 with a defined force.

It is also shown in FIG. 3 that the rolling body holders 7 have a first oblique side wall 14 and a second oblique side wall 15. The first oblique side wall 14 and the second oblique side wall 15 are in this case aligned parallel to one another and also respectively inclined at an angle of approximately 30° with respect to a radial direction of the cage 8. This brings about the effect that raising of the rolling bodies 6 in a radial direction is easier when there is relative rotation of the rotor 4 with respect to the cage 8 in the first direction of rotation than in an opposite second direction of rotation. Thus, in FIG. 3, clockwise rotation of the rotor 4 or counterclockwise rotation of the cage 8 involves a lower expenditure of torque than an opposite relative rotation. The reason for this is that, when the rolling bodies 6 are raised in the rolling body holders 7 by the rotor 4, the elevations between the depressions 5 of the rotor 4 also bring about the effect that the rolling bodies 6 are driven in the relative direction of rotation of the rotor 4. It depends here whether the rolling bodies 6 are faced in this direction of movement by an obliquely "upwardly" inclined side wall or an obliquely "downwardly" inclined side wall, i.e. inclined counter to the direction of movement.

Other typical embodiments have two differently inclined side walls. The arrangement of the side walls in a symmetrical V shape, so that the same torque can be transmitted in both directions of rotation, is likewise possible.

The arrangement shown advantageously achieves the effect that constant or virtually constant mechanical properties of the torque limiter are achieved even over a relatively long service life and, furthermore, it is possible for unscrewing to be performed with a significantly higher torque than screwing in, which is only possible with the maximum torque determined by the torque limiter.

Figure 4:
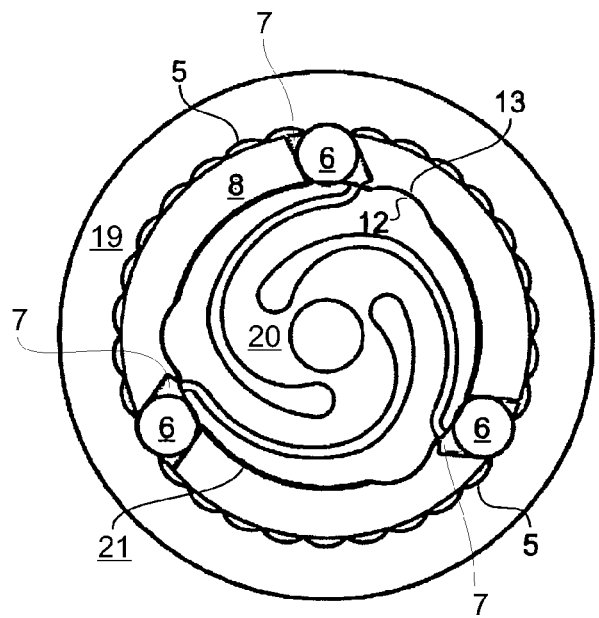
FIG. 4 shows a cross section through another exemplary embodiment of a torque limiter according to the invention.

FIG. 4 shows in a schematic diagram a further embodiment of a torque limiter according to the invention. In the case of the diagram in FIG. 4, the same designations are used for the same or similar parts.

The torque limiter that is represented in FIG. 4 has an inner cage 8 and an outer rotor 19. An inner spring washer 20 with spirally arranged spring arms 21 presses rolling bodies 6 outward in longitudinal grooves of the rotor 19. The spring arms 21 are formed spirally on the spring washer 20. Cams 12 formed on the spring arms 11 and grooves 13 arranged in the cage 8 form an anti-rotation element. The embodiment represented, with the inner rotor 19, has the advantage of a compact form of construction. The remaining construction and the remaining alternatives, for example for pressure-exerting elements, may be provided in a way corresponding to the exemplary embodiment previously described.

The invention claimed is:

1. Torque limiter, in particular for a surgical instrument, comprising:
   a rotor;
   a cage arranged coaxially relative to the rotor, the cage has at least one rolling body holder; and
   a rolling body held in the rolling body holder, wherein the rolling body holder has at least one side wall, which is arranged at an oblique angle to a circumferential direction of the cage further including a pressure-exerting element for pressing the rolling body against the rotor wherein the pressure-exerting element comprises a spring washer having spring arms extending substantially in the circumferential direction.

2. Torque limiter according to claim 1, wherein the rotor comprises a depression, which interacts with the rolling body.

3. Torque limiter according to claim 1, wherein the rolling body is configured as a roller and/or a depression comprises a longitudinal groove in the rotor.

4. Torque limiter according to claim 1, wherein the pressure-exerting element is circular or annular.

5. Torque limiter according to claim 1, wherein the pressure-exerting element is one of a rubber ring.

6. Torque limiter according to claim 1, wherein the cage and the spring washer are held in a fixed angular position relative to one another by an anti-rotation element.

7. Torque limiter according to claim 6, wherein the anti-rotation element comprises a groove which interacts with a cam.

8. Torque limiter according to claim 1, further comprising a second side wall of the rolling body holder which is opposite the first side wall and is aligned substantially parallel to the first side wall.

* * * * *

UNITED STATES PATENT AND TRADEMARK OFFICE
CERTIFICATE OF CORRECTION

PATENT NO. : 8,376,863 B2
APPLICATION NO. : 12/903293
DATED : February 19, 2013
INVENTOR(S) : Ulrich Wernz and Stephan Siebold It is certified that error appears in the above-identified patent and that said Letters Patent is hereby corrected as shown below:

In the Claims:

In column 6, claim 5, line 55, please insert -- and a spring washer -- after the word "ring" and before the ".".

Signed and Sealed this
Twenty-eighth Day of May, 2013

Teresa Stanek Rea
*Acting Director of the United States Patent and Trademark Office*